US00PP17175P2

(12) United States Plant Patent
Carruth

(10) Patent No.: US PP17,175 P2
(45) Date of Patent: Oct. 31, 2006

(54) HYBRID TEA ROSE PLANT NAMED 'WEKLEZPAT'

(50) Latin Name: *Rosa hybrida*
Varietal Denomination: WEKlezpat

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/979,343

(22) Filed: Nov. 1, 2004

(51) Int. Cl.
*A01H 5/00* (2006.01)

(52) U.S. Cl. ..... Plt./130

(58) Field of Classification Search ..... Plt./130
See application file for complete search history.

*Primary Examiner*—Anne Marie Grunberg
*Assistant Examiner*—Annette H Para
(74) *Attorney, Agent, or Firm*—Christie, Parker & Hale, LLP

(57) ABSTRACT

A new variety of Hybrid Tea suitable for garden decoration, having flowers of butter gold blushed pink coloration.

1 Drawing Sheet

Classification: The present invention relates to a new *Rosa hybrida* plant.

Variety denomination: The new plant has the varietal denomination 'WEKlezpat'.

BACKGROUND OF THE INVENTION

This invention relates to a new and distinct variety of Hybrid Tea Rose. It has as its seed parent the variety known as 'HARwelcome' (U.S. Plant Pat. No. 9,161) and as its pollen parent the variety known as 'WEKamanda' (U.S. Plant Pat. No. 9,591).

SUMMARY OF THE INVENTION

Among the features which distinguish the new variety from other presently available and commercial rose cultivars known to the inventor are the following combination of characteristics: its young leaves showing a suffusion of red on the stipule and rachis, its very rough rachis with some small prickles, its entirely smooth peduncle, its dark red suffusion on the inner surface of the sepals that appears as the flower ages and its strong fruity to somewhat spicy fragrance. The plant has an upright moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKlezpat' may be asexually propagated by budding and grafting. The budding and grafting successfully occurred on the plant/rootstock *Rosa hybrida* cv. 'Dr. Huey'.

Comparison with Parents

The new rose may be distinguished from its seed parent, 'HARwelcome' by the following combination of characteristics: whereas 'WEKlezpat' bears very double flowers (about 48 to 72 petals) of butter gold blushed pink coloration, 'HARwelcome' bears double flowers with significantly lesser petalage (about 25 to 30 petals) of blended orange coloration. The new variety is classified as a hybrid tea rose and usually bears its flowers singly, whereas the seed parent is classified as a floribunda rose and usually bears its flowers in clusters of three to four or more per stem.

The new variety may be distinguished from its pollen parent, 'WEKamanda' by the following combination of characteristics: whereas 'WEKlezpat' bears flowers of butter gold blushed pink coloration, 'WEKamanda' bears flowers of yellow gold coloration shaded with green. The pollen parent bears matte foliage, whereas the new variety bears moderately glossy foliage. 'WEKlezpat' has an upright moderately spreading tall growing habit (about 152 to about 170 cm. in height), whereas 'WEKamanda' has a bushy upright medium height significantly shorter growing habit (about 95 to about 130 cm. in height).

Comparisons with the Closest Commercially Available Cultivar

The new rose may be distinguished from its closest commercially available cultivar, 'JACfrens', by the following combination of characteristics: whereas 'WEKlezpat' bears flowers of butter gold blushed pink coloration, 'JACfrens' bears flowers of bright, early yellow changing to a blended coloration as it ages. 'WEKlezpat' bears very double flowers (about 48 to 72 petals) of average size (about 7.7 to about 11.8 cm. in diameter), while 'JACfrens' bears double flowers with significantly lesser petalage (about 35 to 40 petals) and of significantly larger dimension (about 12 to about 13 cm. in diameter).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers singly. Flowers are borne on strong short to medium length stems (about 18 to about 48 cm.). Outdoors, the plant blooms abundantly and nearly continuously during the growing season. The flowers have a strong fruity to somewhat spicy fragrance.

BUD

The peduncle is about 3.1 to about 6.5 cm. in length, of average caliper (about 0.3 to about 0.5 cm. in diameter), and usually erect. It is entirely smooth, with some hairs and sometimes very few stipitate glands. Peduncle color is between 144A and 147C often moderately suffused, especially on the side exposed to the sun, with between 187B and 187A.

Before the calyx breaks, the bud is about 1.4 to about 2.1 cm. in diameter at the widest point, about 1.7 to about 2.5 cm. in length, and pointed to somewhat ovoid in shape with a moderately conspicuous neck. The surface of the bud bears some foliaceous appendages and hairs, usually with slender entire foliaceous parts extending beyond the tip of the bud about ¼ or more of its length. Bud color is between 146B and 147C often moderately suffused, especially on the side exposed to the sun, with between 187A and 187B.

The sepals are about 2.3 to about 3.8 cm. in length and about 0.7 to about 1.1 cm. in width at the widest point. The outer surface color of the sepal is between 146B and 147C often moderately suffused, especially on the side exposed to the sun, with between 187A and 187B. The inner surface color of the sepal is between 138B and 137B. After the sepals open and as the flower ages, the inner surface color often becomes heavily suffused with between 187A and 187B. The inner surface is covered with fine wooly tomentum; sepal margins are lines with many stipitate glands and some hairs.

As the petals open (after the calyx breaks), the bud is about 2.2 to about 3.5 cm. in diameter at the widest point, about 2.6 to about 4.3 cm. in length, and ovoid in form. On the under and upper surfaces of the newly opened petals, the color at the base of the petal is between 12A and 20B that gradually suffuses toward the center of the petal to between 24B and 26B, often heavily blushed with between 187A and 60A. There is no visible change in coloration at the point where the petal attaches.

BLOOM

When fully open, the bloom ranges from about 7.7 to about 11.8 cm. in diameter. Petalage is very double with about 48 to 72 petals and about 7 to 10 petaloids irregularly arranged. When partially open, the bloom form is moderately high centered to cupped, and the petals are moderately spiraled to cupped with petal edges somewhat reflexed outward. When fully open, the bloom form is very cupped, and the petals are loosely cupped with petal edges moderately reflexed outward.

PETALS

The substance of the petals is somewhat heavy and of moderately thin thickness, with upper surfaces slightly satiny and under surfaces somewhat shiny. The outer petals are broadly obovate in shape with rounded apices. The inner petals are moderately obovate to somewhat oblanceolate in shape with rounded apices. The petals are about 2.5 to about 4.7 cm. in length and about 1.5 to about 4.2 cm. in width at the widest point. Petal margins are entire.

NEWLY OPENED FLOWER

On the under and upper surfaces of the outer petals, the color at the base of the petals is between 12B and 20B, gradually suffusing toward the center of the petals to between 16C and 27D and often moderately blushed toward the petal edge with between 33D and 60A. There is no visible change in coloration at the point where the petal attaches.

On the under and upper surfaces of the intermediate and inner petals, the color at the base of the petals is between 12A and 20B, gradually suffusing toward the center of the petals to between 23C and 22C and sometimes moderately blushed toward the petal edges with between 33D and 60A. There is no visible change in coloration at the point where the petal attaches.

The blushed coloration is usually more evident on the upper side of the outermost petals.

The general tonality of the newly opened flower is between 12A and 20B at the base of the petal, gradually suffusing toward the center of the petal to between 23C and 22C and sometimes moderately blushed toward the petal edge with between 33D and 60A.

THREE-DAY-OLD FLOWER

The under and upper surface color of the outer, intermediate and inner petals is between 10B and 20B, often moderately blushed toward the petal edge with between 43C and 60A. At the point where the petal attaches, there is a moderately small zone of between 12B and 20B.

The blushed coloration is usually more evident on the upper side of the outermost petals.

The general tonality of the three-day-old flower is between 10B and 20B, often moderately blushed toward the petal edge with between 43C and 60A.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 100) and are arranged regularly about the pistils; a few are mixed with petaloids. The filaments are of moderately short to medium length (about 0.3 to about 0.8 cm.), most with anthers. Filaments are between 12A and 13B in color sometimes lightly blushed at the base with near 53B. The anthers are of medium size for the class and all open approximately at the same time. Anther color is between 21B and 16D when immature and between 202A and 167A at maturity. Pollen is abundant.

FEMALE REPRODUCTIVE ORGANS

Pistils vary in number (average about 130). The styles are moderately even, average in length (about 0.4 to about 0.8 cm.), moderately thin in caliper, and loosely separated to somewhat bunched. Stigma color is between 9C and 10A. Style color is between 150C and 154C usually lightly suffused near the top with between 53B and 53C. Ovaries are usually all enclosed in the calyx.

Hips have not been observed on this variety when grown in Upland, Calif.

FOLIAGE

The compound leaves are usually comprised of three to seven or more leaflets and are borne abundantly. The seven-leaflet leaves are about 11.7 to about 15.5 cm. in length and about 8.5 to about 11.4 cm. in width at the widest point, leathery to moderately crisp in texture, and moderately glossy in finish. The terminal leaflets are about 4.3 to about 6.5 cm. in length and about 3.0 to about 4.3 cm. in width at the widest point, shaped obovate to somewhat oval with moderately acute apices and rounded bases. Their margins are usually simply serrate.

The upper surface color of the mature leaf is between 147A and 139A. The under surface color of the mature leaf is between 147B and 148D. The upper surface color of the young leaf is between 146A and 146B, usually heavily suffused with between 187A and 183A. The under surface color of the young leaf is between 146B and 148D, usually heavily suffused with between 187B and 187A.

The rachis is somewhat light in caliper and very rough. The upper side is shallowly grooved with very few hairs and some stipitate glands on the edges of the grooves. The under side of the rachis is very rough with few stipitate glands and some small prickles. The rachis color is between 147A and 146B usually heavily suffused especially on the young leaves with between 187A and 183A.

The stipules are about 1.1 to about 2.1 cm. in length and of somewhat narrow to medium width (about 0.5 to about 0.9 cm.) with medium length straight points that usually turn out at an angle of more than 45 degrees and sometimes recurve toward the stem. The stipule color is between 147B and 146B sometimes moderately suffused especially on the under side of the young leaves with between 187A and 183A.

The petiole is about 0.8 to about 1.1 cm. in length and about 0.1 to about 0.15 cm in diameter at the widest point. The petiole color is between 147A and 146B usually heavily suffused especially on the young leaves with between 187A and 183A.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has an upright moderately spreading tall growing habit (about 152 to about 170 cm. in height and about 62 to about 90 cm. spread at the widest point), with full branching. It displays moderately vigorous growth and the canes are of medium caliper for the class.

The color of the major stems is between 147B and 146B. They bear many large prickles that are about 0.7 to about 1.1 cm. in length. The large prickles are almost straight and angled slightly downward with a moderately long broad oval base; prickle color is between 177B and 165A. The major stem bears some small prickles of similar shape and coloration.

The color of the branches is between 146B and 147C. They bear many large prickles which are of similar size and shape to the large prickles on the major stems; prickle color is between 160B and 162C. The branches bear some small prickles of similar shape and coloration.

The color of the new shoots is between 144B and 147C often moderately suffused with between 187B and 187A. They bear many large prickles which are of similar size and shape to the large prickles on the major stems; prickle color is between 146C and 144B usually moderately suffused with between 187A and 187C. The shoots bear some small prickles of similar shape and coloration.

I claim:

1. A new and distinct Hybrid Tea rose plant of the variety substantially as described and illustrated herein.

* * * * *

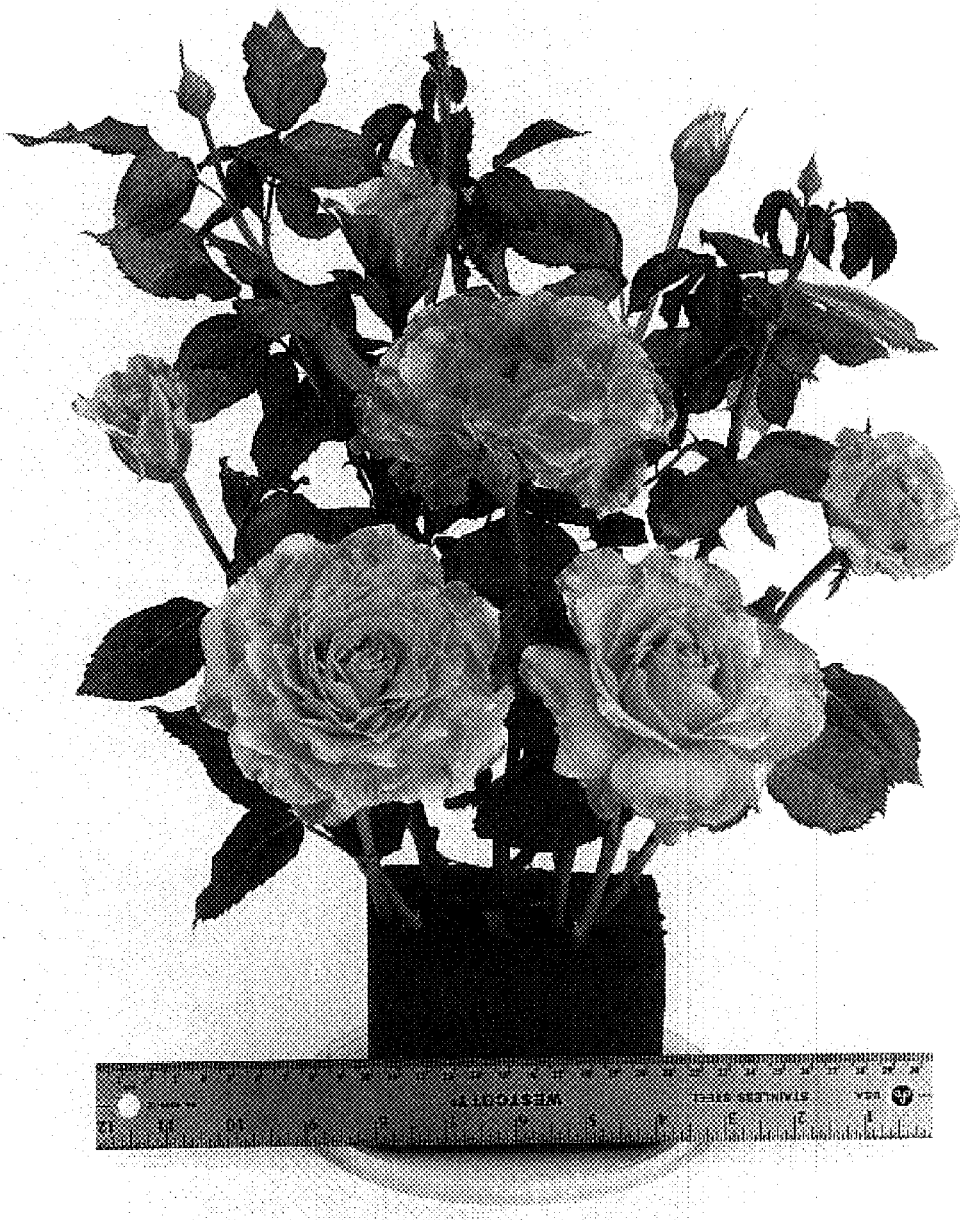
WESTON
STAINLESS STEEL